United States Patent [19]

Varwig et al.

[11] Patent Number: 4,562,254

[45] Date of Patent: Dec. 31, 1985

[54] PREPARATION OF 5-FLUORO-2-PHENYL-4H-3,1-BENZOXA-ZIN-4-ONES

[75] Inventors: Jürgen Varwig, Heidelberg; Gerhard Hamprecht, Weinheim; Wolfgang Rohr, Wachenheim, all of Fed. Rep. of Germany

[73] Assignee: BASF Aktiengesellschaft, Fed. Rep. of Germany

[21] Appl. No.: 655,726

[22] Filed: Sep. 28, 1984

[30] Foreign Application Priority Data

Sep. 30, 1983 [DE] Fed. Rep. of Germany ....... 3335456
Mar. 6, 1984 [DE] Fed. Rep. of Germany ....... 3408154

[51] Int. Cl.$^4$ ............................................. C07D 265/10
[52] U.S. Cl. ..................................... 544/92; 260/384; 549/241; 549/246
[58] Field of Search ......................................... 544/92

[56] References Cited

U.S. PATENT DOCUMENTS 4,315,766 2/1982 Hamprecht et al. ................. 71/88
4,359,428 11/1982 Jacobs et al. .......................... 260/465

OTHER PUBLICATIONS

Houben–Weyl, Methoden der Organischen Chemie, 4th Edition, vol. V/3, pp. 160, et seq.
Finger et al, J. Amer. Chem. Soc., 81 (1959), 2674.

Primary Examiner—Richard L. Raymond
Attorney, Agent, or Firm—Keil & Weinkauf

[57] ABSTRACT

5-Fluorobenzoxazinones (I)

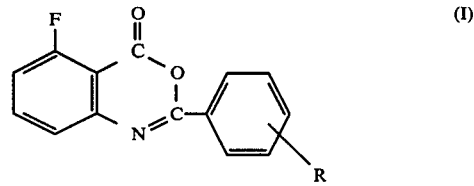

where R is hydrogen, halogen, $C_1$–$C_3$-alkyl, or trifluoromethyl, trifluoromethoxy, chlorodifluoromethoxy, difluoromethoxy, tetrafluoroethoxy, trifluoromethylmercapto or chlorodifluoromethylmercapto in the m- or p-position, are prepared by reacting the corresponding benzoxazinone (II)

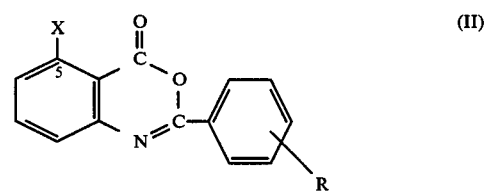

in particular one which is 5-chloro-substituted or 5-bromo-substituted, with a fluoride, in particular potassium fluoride, in the presence or absence of a solvent, by a process in which the reaction is carried out in the absence of water or using previously dried starting materials, and in the presence or absence of a decomposition inhibitor, drying preferably being carried out by treatment with an acid halide, e.g. thionyl chloride, and the inhibitor used being a metal iodide, e.g. sodium iodide, or iodine.

18 Claims, No Drawings

PREPARATION OF 5-FLUORO-2-PHENYL-4H-3,1-BENZOXAZIN-4-ONES

5-Fluoro-2-phenyl-4H-3,1-benzoxazin-4-ones possess herbicidal activity and are distinguished by high activity and a broad action spectrum (German Laid-Open Applications DOS 2,914,915, DOS 3,000,309 and DOS 3,037,970). Examples of typical compounds of this type are those of the general formula (I)

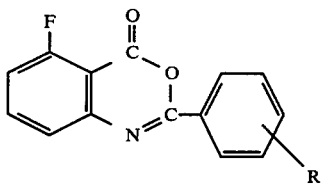

where R is hydrogen, halogen, $C_1$-$C_3$-alkyl, or trifluoromethyl, trifluoromethoxy, chlorodifluoromethoxy, difluoromethoxy, tetrafluoroethoxy, trifluoromethylmercapto or chlorodifluoromethylmercapto in the m- or p-position.

The compounds (I) are usually prepared by reaction of 6-fluoroanthranilic acid with an unsubstituted or appropriately substituted benzoyl halide, and cyclization (see above).

This method is uneconomical since the 6-fluoroanthranilic acid required cannot yet be prepared in a sufficiently economical manner (German Laid-Open Application DOS 3,044,904 and EP-A 55,629).

We have found a process which starts from an appropriate 4H-3,1-benzoxazin-4-one which is substituted in the 5-position and is of the formula (II)

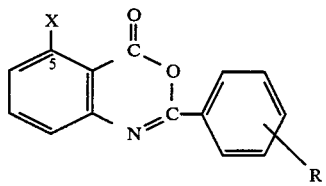

where X is preferably chlorine or bromine but may furthermore be iodine, nitro, mesyl or tosyl.

In this context, the following preliminary remarks may be made:

According to Houben-Weyl, Methoden der Organischen Chemie, 4th Edition, Vol. V/3, page 160 et seq., aromatically bonded chlorine can be exchanged for fluorine only if its bond is weakened by two electron-attracting substituents in the o- and p-positions. In the case of aromatics substituted by carboxylic ester groups, the halogen exchange can be carried out only if, for example, an additional nitro group is also present.

This rule is underlined by the observation that, even in the case of 2-chloropyridines, the halogen exchange is possible only if the bond to chlorine is weakened by an o- or p-nitro group. For example, certain 2- or 6-fluoronitropyridines can be obtained in this manner (J. Amer. chem. Soc. 81 (1959), 2674). The nitrogen atom of the pyridine ring does not itself effect sufficient weakening of the bond to the chlorine atom in the 2-position; as is well known to a skilled worker, 2-chloro- or 3-bromopyridine cannot be converted to 2-fluoropyridine. Furthermore, the small activating effect of an m-nitro group is evident from the fact that the conversion of 2-chloro-4-nitropyridine with potassium fluoride at 160° C. to the fluorine compound is not possible either in dimethylformamide or in dimethyl sulfoxide (Houben-Weyl, loc. cit., page 165).

It has also been disclosed that, in the case of halogen exchange in substituted aromatic carboxylic acid derivatives, chlorine atoms in the o-position lead to carbonyl decomposition reactions. For example, Odinokov et al. (CA. 69, 187977) state that, when 3,6-dichlorophthalic anhydride is reacted with potassium fluoride in the course of 3 hours at 190°-200° C., 3,6-difluorophthalic anhydride is formed in only 54% yield, whereas, at from 240° to 245° C. and in the course of 8 hours, the bislactone of α,α'-dihydroxy-3,6,3', 6'-tetrafluorodiphenylmethane-2,2'-dicarboxylic acid is formed as the principal product in a yield of 52%, carbon dioxide being eliminated. At a still higher temperature, i.e. 330°-340° C., carbon dioxide is once more eliminated with formation of a 1,4,5,6-tetrafluoroanthraquinone.

It has also been disclosed that potassium fluoride on the one hand nucleophilically attacks sulfite esters (J. Org. Chem. 31 (1966) 842) and acrylates (J. Chem. Soc. 1962, 1056 and J. Chem. Soc. Perkin Trans. I, 1978, 269) with elimination of the acyl group, and on the other hand also readily decarboxylates aromatic carboxylic acids, e.g. anthranilic acid (C.A. 42, 4924 g). All of these side reactions have an adverse effect on the halogen exchange reaction of, for example, 5-chloro-substituted 2-phenyl-4H-3,1-benzoxazin-4-one derivatives with potassium fluoride, and give substantial amounts of decomposition products, as shown in the equation below:

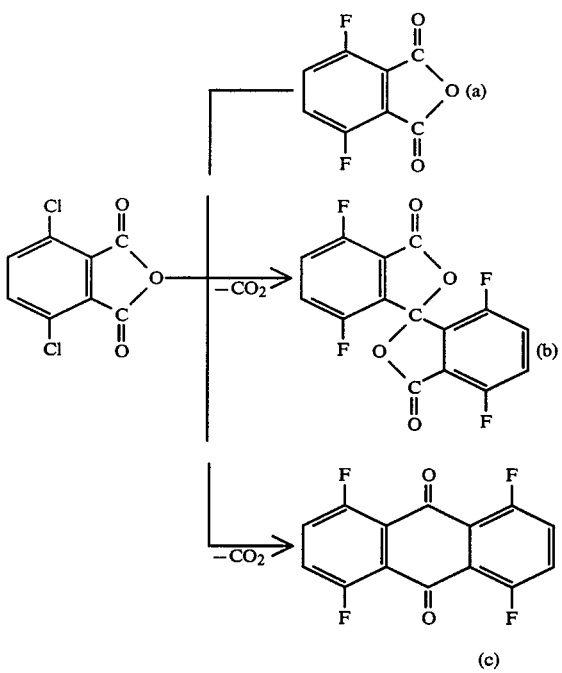

| | | |
|---|---|---|
| 5 hours | 190–200° C. | 54 (a) |
| 8 hours | 240–245° C. | 52 (b) |
| 2.5 hours | 330–340° C. | 30 (c) |

We have found that 5-fluoro-2phenyl-4H-3,1-benzoxazin-4-ones of the formula (I)

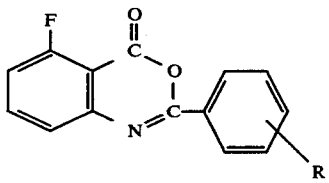

(I)

defined above can be obtained if the corresponding 2-phenyl-4H-3,1-benzoxazin-4-one (II) which is substituted by chlorine, bromine, iodine, nitro, mesyl or tosyl is reacted with an alkali metal fluoride in the absence of water.

The starting compounds can be reacted with a stoichiometric amount or an excess of an (alkyl)ammonium fluoride or alkali metal fluoride, preferably with potassium fluoride, advantageously in an amount of from 1 to 5, preferably from 1 to 1.5, in particular from 1 to 1.15, moles per mole of benzoxazinone.

The reaction in the presence of a solvent gives a good yield when carried out at about 160°–250° C., preferably 180°–230° C., under atmospheric or, if required, superatmospheric pressure, either batchwise or continuously. Above this temperature range, the yields deteriorate. A suitable solvent is, for example, dimethylformamide, dimethyl sulfoxide, a polyethylene glycol dialkyl ether, acetonitrile, hexamethylphosphorotriamide, or an open-chain or cyclic sulfone, e.g. sulfolane. If it is desired to carry out the reaction in the absence of a solvent, it is necessary to use a temperature above 250° C., e.g. from 300° to 500° C.; contrary to expectations, the starting materials and end products withstand this temperature in this case.

When a solvent is employed, it is very advantageous to add a solubilizer, particularly where potassium fluoride is used. Examples of suitable compounds are crown ethers, polyethylene glycols and their derivatives. Cesium fluoride is relatively readily soluble. Usually, however, potassium fluoride or ammonium fluoride is preferably used, and a sulfone, e.g. sulfolane, is employed as the solvent. If cesium fluoride is used, it is possible to dispense with a solubilizer and, for economic reasons, to extend this with another fluoride or to regenerate it.

Another improvement in the process is achieved by carrying out the reaction in the presence of a metal iodide or of iodine, which inhibits decomposition reactions of the heterocyclic structure which accompany the halogen exchange.

The amount of iodide or iodine is, for example, from 1 to 10, in particular from 0.1 to 5, mole %, based on benzoxazinone.

Anhydrous reaction conditions are a prerequisite for the process according to the invention.

Prior thorough drying of the starting materials and, where relevant, of the solvent is therefore important with regard to the technical feasibility. It is desirable to distil the solvents or to add dehydrating agents, and in particular to dry the fluorinating agent thoroughly and to disperse it finely in the reaction medium.

Particular attention must be paid to the drying procedure, it being advantageous with regard to the isolation of the desired products if the drying agents used do not leave behind any residues which cannot be vaporized. Halides of sulfurous acid or carbonic acid, in particular thionyl chloride, are preferred.

Although it is frequently sufficient to dry the fluorine salt by an appropriate pretreatment, the most reliable method is to carry out the reaction in the presence of the drying agent. If the procedure is restricted to a pretreatment, the latter can be carried out at below 120° C.

In general, the following procedure can be employed:

The dry benzoxazinone, if required an iodide or iodine, and thoroughly dried, finely powdered potassium fluoride are reacted at a sufficiently high temperature in the presence (taking into account the version in which the benzoxazinone is vaporized) or absence of a solvent and in the presence or absence of a catalyst for about 2 minutes to 24 hours, depending on the procedure, and the insoluble inorganic residue is separated off and can be washed. Where a solvent, such as sulfolane, is employed, it is distilled off. The product can, if required, be washed with, for example, acetic acid and/or acetic anhydride, ethanol, ether, water, acetone or methylene chloride, or can be recrystallized. A particularly preferred method of purification comprises distilling the product under reduced pressure and at elevated temperatures.

In the novel process, the starting materials required are, in particular, 5-chloro- or 5-bromo-substituted 2-phenyl-4H-3,1-benzoxazin-4-ones of the formula II, e.g. 5-chloro-2-phenyl-4H-3,1-benzoxazin-4-one, 5-chloro-2-(3'-trifluoromethylphenyl)-4H-3,1-benzoxazin-4-one, 5-chloro-2-(3'-chlorodifluoromethoxyphenyl)-4H-3,1-benzoxazin-4-one, 5-chloro-2-(3'-trifluoromethoxyphenyl)-4H-3,1-benzoxazin-4-one, 5-chloro-2-(3'-difluoromethoxyphenyl)-4H-3,1-benzoxazin-4-one, 5-chloro-2-(3'-tetrafluoroethoxyphenyl)-4H-3,1-benzoxazin-4-one, 5-chloro-2-(3'-trifluoromethylmercaptophenyl)-4H-3,1-benzoxazin-4-one, 5-chloro-2-(3'-chlorodifluoromethylmercaptophenyl)-4H-3,1-benzoxazin-4-one, 5-chloro-2-(4'-chlorodifluoromethoxyphenyl)-4H-3,1-benzoxazin-4-one, 5-chloro-2-(4'-chlorodifluoromethylmercaptophenyl)-4H-3,1-benzoxazin-4-one, 5-chloro-2-(4'-tetrafluoroethoxyphenyl)4H-3,1-benzoxazin-4-one or the corresponding 5-bromo compounds; these are advantageously pretreated with thionyl chloride or phosgene in a first stage, in the presence of an aliphatic sulfone at as high as 120° C. In general, a temperature of less than 120° C. is sufficient for the pretreatment. Where the main reaction is carried out in an aliphatic sulfone, the solvent and the acid halide need not be removed.

Examples of suitable aliphatic sulfones are the compounds of the formula (III)

(III)

where $R^1$ and $R^2$ are identical or different and are each an aliphatic radical, preferably alkyl of 1 to 8, in particular 1 to 4, carbon atoms, or $R^1$ and $R^2$ together form an alkylene radical of 4 or 5 carbon atoms. Examples of very useful solvents of the stated type are dimethyl sulfone, diethyl sulfone, dipropyl sulfone, diisopropyl sulfone, dibutyl sulfone, diisobutyl sulfone, methyl ethyl sulfone, tetramethylene sulfone (sulfolane) and pentamethylene sulfone, sulfolane being preferred. In general, the solvent is used in as much as a 10-fold excess based on weight, and is generally present in the reaction mixture in an amount of from 100 to 400 percent by weight, based on starting material II. The acid chloride is advantageously used in an amount of from 1 to 20, preferably from 2 to 12, percent by weight, based on the sulfone.

Examples of suitable catalysts for the pretreatment are N,N-disubstituted carboxamides of 3 to 10 carbon atoms, e.g. N,N-dimethylformamide, N,N-dimethylacetamide, N,N-diethylformamide, N,N-di-n-propylacetamide, N-methyl-N-ethylformamide or N,N-diisopropylacetamide. The catalyst is advantageously used in an amount of from 0.2 to 2 per cent by weight, based on the acid halide.

If necessary, it is also possible for the alkali metal fluoride to be pretreated in the same manner with one of the above acid halides, if appropriate in an inert solvent having a boiling point as high as 120° C. Advantageously, the alkali metal fluoride is suspended in the excess solvent, and the acid halide is then added, advantageously in an amount as high as 100, preferably from 2 to 30, percent by weight, based on the alkali metal fluoride. The mixture is then stirred while being heated, for example to 120° C., advantageously from 50 to 110° C., in particular from 70 to 100° C., after which it is evaporated down under from 10 to 30 mbar. The treatment usually lasts no more than 2 hours. The potassium fluoride treated in this manner is then added to a mixture of untreated or pretreated starting material II with the aliphatic sulfone. However, it is also possible for the mixture of the starting material II with the aliphatic sulfone to be pretreated, as described, with an acid chloride, after which, when evolution of gas is complete, dry, untreated alkali metal fluoride, metal iodide and/or iodine are added.

The starting material (benzoxazinone; II), the sulfone, the metal iodide and the acid halide can in principle be mixed with one another in any sequence. Advantageously, however, the starting material II is first mixed with the metal iodide and the sulfone III, and, if required, with a catalyst, at from 30 to 40° C., after which the acid halide is added to the stirred mixture and heating is advantageously continued until evolution of gas is no longer observed. Excess acid halide can be removed, for example, by flushing with nitrogen or the like, or by employing reduced pressure.

However, the metal iodide and, owing to its volatility, particularly elemental iodine are advantageously added only after the starting material II in the sulfone has been treated with the acid halide.

In a particularly advantageous procedure, the carefully dried starting material II, potassium fluoride, sulfolane, metal iodide and/or iodine are mixed with the acid halide, after which the reaction is carried out. In this procedure, it is also possible to add the iodide or iodine at a later stage in the course of the reaction, but no later than when the reaction is half complete, i.e. after half the reaction time has elapsed.

Finally, in order to avoid unnecessary fluoride losses, it is advantageous if the remaining amount of acid halide does not exceed from 1 to 5 mole per cent, based on the alkali metal fluoride in the actual reaction. As a rule, the residual amount of acid halide still present after the pretreatment of the mixture of starting material II and aliphatic sulfone and after an inert gas has been blown in or the pressure reduced to 10-30 mbar is sufficient for the treatment of the alkali metal fluoride which is added to initiate the actual reaction.

Regarding the actual reaction, where this has not already been described, the following remarks may be made.

The halogen exchange reaction proceeds rapidly even in the absence of a catalyst. However, where a solvent is employed, the reaction can be accelerated by adding a crown ether or a cryptand. These are complex organic ligands which are particularly useful for binding alkali metals. Crown ethers are cyclically bonded neutral ethylene glycol ethers. The cryptands provide a three-dimensional envelope. The preparation of such substances is described in Kontakte (1977), pages 11–31 and 36–48. Examples of crown ethers are the following compounds: 12-crown-4, 2,4,6,8-methyl-12-crown-4, 14-crown-4, dibenzo-14-crown-4, dibutylbenzo-14-crown-4, dicyclohexyl-14-crown-4, 15-crown-5, 1,2-benzo-15-crown-5, 1,2-butylbenzo-15-crown-5, 1,2-cyclohexyl-15-crown-5, dibenzo-15-crown-5, 16-crown-5, dibenzo-16-crown-5, 18-crown-5, dibenzo-18-crown-5, 18-crown-6, benzo-18-crown-6, cyclohexyl-18-crown-6, dibenzo-18-crown-6, dicyclo-hexyl-18-crown-6, tribenzo-18-crown-6, dinaphtho-18-crown-6, 19-crown-6, dibenzo-19-crown-6, 20-crown-7, dibenzo-5-oxy-20-crown-7, 21-crown-7, dibenzo-21-crown-7, dicyclohexyl-21-crown-7, 24-crown-8, dibenzo-24-crown-8, dicyclohexyl-24-crown-8, tetrabenzo-24-crown-8, 30-crown-10, 40-crown-20, aza-18-crown-6, dibenzo-aza-18-crown 6, diaza-18-crown-6, dibenzo-diaza-18-crown-6, 1,4-dithia-15-crown-5, 1,4-dithia-18-crown-6, 1,7-dithia-benzo-18-crown-6, 1,10-dithia-benzo-18-crown-6 and 1,7,10,16-tetrathia-18-crown-6.

The catalysts are advantageously used in an effective amount as high as 0.5, in particular from 0.1 to 0.3, mole per cent, based on starting material II.

After the reaction, which is complete after about 4–12 hours, the mixture is worked up in a conventional manner, for example by filtration, distillation of the filtrate and washings, washing the solid product, etc.

When the procedure is carried out in the absence of a solvent, the following is important.

Advantageously, the starting material II is initially taken in the molten state and is then mixed with the dry fluoride ride salt and, where relevant, a metal iodide. However, the starting material II, the fluoride salt and, where relevant, a metal iodide can also be fed in uniformly via suitable metering apparatuses, and mixed with one another. If the reaction is carried out at above the boiling point of the end product I, the fluoride salt is advantageously initially taken, for example on a carrier or in a fluidized bed, and the starting material II is then metered in as a gas, the end product being removed from the reaction space by distillation.

If the fluoride salt contains water, it is first dried under the reaction conditions, if necessary under reduced pressure, and then the starting material II is metered in.

If the fluoride salt and the starting material II are metered in uniformly, further stirring of the reaction mixture after initial thorough mixing is not required in order to complete the reaction. The reaction can therefore be carried out by a type of baking process or in a tube reactor.

The reaction temperature can be adapted to certain conditions relating to apparatus and possible methods of heating, but advantageously should be not less than 290°–300° C. In this lower temperature range, correspondingly long reaction times have to be chosen, for example from 18 to 24 hours at 300° C. At a middle temperature, e.g. 380° C., the reaction time is about 25–35 minutes, and it becomes correspondingly shorter at still higher temperatures.

In an advantageous embodiment of the novel process, the end product is distilled off directly from the reaction mixture, at the rate at which it is formed.

In general, for example where the starting material II is metered in a molten state, a reaction temperature of from 320° to 410° C. is chosen; if the starting material II is introduced in the form of a gas, a still higher reaction temperature can be chosen, the reaction being carried out under atmospheric or reduced pressure.

After the reaction, the mixture is worked up in a conventional manner, for example by distillation, or by washing the solid product to remove the metal salts.

EXAMPLE 1

6.0 kg of 5-chloro-2-phenyl-4H-3,1-benzoxazin-4-one and 2.3 kg of thoroughly dried and finely powdered potassium fluoride in 18 l of dry sulfolane are stirred for 11 hours at from 200° to 220° C. The mixture is filtered at 100° C. and washed, and the solvent is distilled off.

The residue is distilled at 200° C. and under 5 mbar, and is washed with water. 3,215 g of 5-fluoro-2-phenyl-4H-3,1-benzoxazin-4-one of melting point 162°–164° C. are obtained.

Compounds which can be prepared from the corresponding 5-chloro compound in a similar manner include 5-fluoro-2-(3'-trifluoromethylphenyl)-4H-3,1-benzoxazin-4-one, 5-fluoro-2-(4'-trifluoromethylphenyl)-4H-3,1-benzoxazin-4-one, 5-fluoro-2-(3'-fluorophenyl)-4H-3,1-benzoxazin-4-one, 5-fluoro-2-(3'-chlorophenyl)-4H-3,1-benzoxazin-4-one, 5-fluoro-2-(4'-trifluoromethoxyphenyl)-4H-3,1-benzoxazin-4-one, 5-fluoro-2-(3'-trifluoromethoxyphenyl)-4H-3,1-benzoxazin-4-one, 5-fluoro-2-(3'-difluorochloromethoxyphenyl)-4H-3,1-benzoxazin-4-one, 5-fluoro-2-(4'-difluorochloromethoxyphenyl)-4H-3,1-benzoxazin-4-one, 5-fluoro-2-(4'-tetrafluoroethoxyphenyl)-4H-3,1-benzoxazin-4-one and 5-fluoro-2-(3'-tetrafluoroethoxyphenyl)-4H-3,1-benzoxazin-4-one.

EXAMPLE 2

4 kg of thionyl chloride are added to a stirred mixture of 20 kg of 5-chloro-2-phenyl-4H-3,1-benzoxazin-4-one and 68 kg of sulfolane at 40° C. The mixture is heated to 90° C., and stirred at this temperature until evolution of gas is complete, this taking 45 minutes. Excess thionyl chloride is then stripped off in the course of 12 minutes under reduced pressure from a water pump, a temperature of 100° C. finally being achieved. At this temperature, 6.8 kg of potassium fluoride are then introduced. While the course of the reaction is being monitored by gas chromatography, the mixture is stirred at 215° C. until the degree of conversion reaches 96%, which takes 12 hours.

The mixture is cooled to 40° C. and filtered under suction, the residue is washed with methylene chloride, and 8.3 kg of predominantly inorganic salts are isolated. The filtrate is freed from methylene chloride in a rotary evaporator at 50° C./12 mbar, and then freed from sulfolane by distillation at 82°–87° C./0.3 mbar. The residue is then distilled over a heated bridge at a bath temperature as high as 220° C./0.3 mbar and then triturated with water, and the product is filtered off under suction and dried. 13.25 kg of a virtually colorless product having a melting point of 154°–160° C. and consisting of 12.75 kg of 5-fluoro- and 0.5 kg of 5-chloro-2-phenyl-4H-3,1-benzoxazin-4-one are obtained.

The sulfolane distilled off contains a further 3 kg of 5-fluoro-2-phenyl-4H-3,1-benzoxazin-4-one. The total yield of the fluorine compound is thus 13 kg (more than 65% of theory). For purposes of crop protection, further purification is not required, since the corresponding chlorine compound, which is less active, is not troublesome.

EXAMPLE 3

(a) 50 g of thionyl chloride are run into a mixture of 500 g of potassium fluoride and 1 kg of 1,2-dichloroethane, and the mixture is stirred for 25 minutes at 80° C. The solvent and excess thionyl chloride are removed under 15 mbar in a rotary evaporator. The remaining potassium fluoride contains 32.5% of fluorine (calculated: 32.7%) and 0.3% of chlorine. (b) 8 g of the potassium fluoride treated in this manner are added, at 50° C., to a stirred mixture of 75 g of sulfolane and 20 g of 5-chloro-2-phenyl-4H-3,1-benzoxazin-4-one, after which stirring is continued for 11 hours at 220° C.. Working up as described in Example 2 gives 9.6 g of predominantly inorganic salts, 73 g of sulfolane, 14 g of a virtually colorless distillate and 4 g of distillation residue. The distillate is triturated with water, and the product is filtered off under suction and dried to give a mixture of 13 g of 5-fluoro-and 0.52 g of 5-chloro-2-phenyl-4H-3,1-benzoxazin-4-one having a melting point of 156°–160° C. The sulfolane distilled off contains a further 0.24 g of 5-fluoro-2-phenyl-4H-3,1-benzoxazin-4-one, and the total yield is therefore 13.24 g (70.7% of theory).

EXAMPLE 4

A mixture of 20 g of 5-chloro-2-phenyl-4H-3,1-benzoxazin-4-one, 68 g of sulfolane, 0.8 g of sodium iodide and 5 g of thionyl chloride is stirred for 40 minutes at 95°–100° C., after which it is brought to a reduced pressure of 26 mbar at 98° C. for 20 minutes. 6.76 g of potassium fluoride treated with thionyl chloride (Example 3a) are then added, under a layer of nitrogen, and stirring is continued for 5 hours at 220° C. A further 1.24 g of potassium fluoride treated with thionyl chloride are then added, and, while the course of the reaction is being monitored by gas chromatography, stirring is continued at 220° C. until the degree of conversion reaches 97%; this takes 7.5 hours.

The reaction mixture is diluted with methylene chloride and separated off from the predominantly inorganic precipitate (10.2 g). The filtrate is freed from methylene chloride at 50° C./12 mbar in a rotary evaporator, after which it is freed from sulfolane (63.7 g) at 81°–86° C./0.2 mbar in a distillation apparatus. The residue is then distilled over a heated bridge at a bath temperature as high as 220° C./0.2 mbar, 19 g of virtually colorless product passing over together with residual sulfolane. Washing with water, filtering under suction and drying give 14.9 g of a product which has a melting point of 156°–161° C. and consists of 14.4 g of 5-fluoro and 0.5 g of 5-chloro-2-phenyl-4H-3,1-benzoxazin-4-one. The sulfolane distilled off contains a further 0.29 g of 5-fluoro-2-phenyl-4H-3,1-benzoxazin-4-one, and the total amount of fluorine compound formed is thus 14.7 g, i.e. 78.5% of theory. The aqueous filtrate from washing is evaporated down, 3.8 g of 99% pure (gas chromatography) sulfolane being recovered.

EXAMPLE 5

A mixture of 20 g of 5-chloro-2-phenyl-4H-3,1-benzoxazin-4-one, 68 g of sulfolane (distilled over calcium hydride), 6.76 g of potassium fluoride (dried overnight at 150° C. in a drying oven under reduced pressure), 0.25 g of iodine and 0.05 g of thionyl chloride is stirred for 5.5 hours at 220° C., after which a further 1.24 g of potassium fluoride and 0.25 g of iodine are added and stirring is continued for a further 7.5 hours at 220° C. Working up as described in Example 1 gives 10 g of predominantly inorganic salts, 64.5 g of sulfolane and a mixture of 13.9 g of 5-fluoro- and 0.6 g of 5-chloro-2-phenyl-4H-3,1-benzoxazin-4-one of melting point 155°–159° C. The sulfolane distilled off contains a further 0.28 g of 5-fluoro-2-phenyl-4H-3,1-benzoxazin-4-one; the total amount is 14.2 g, i.e. 75.8% of theory.

EXAMPLE 6

A mixture of 20 g of 5-chloro-2-phenyl-4H-3,1-benzoxazin-4-one, 68 g of sulfolane and 5 g of thionyl chloride is stirred for 30 minutes at 100° C., after which the pressure is reduced to 19 mbar at 110° C. for 30 minutes. 6.35 g of potassium fluoride which has been dried by heating and 0.066 g of thionyl chloride are added, under a layer of nitrogen, and stirring is continued for 15 minutes at 240° C. 0.25 g of iodine are added, after which stirring is continued for a further 3.5 hours at 240°C.

Working up the reaction mixture as described in Example 1 gives 8.0 g of predominantly inorganic salts, 67.5 g of sulfolane and a mixture of 13.1 g of 5-fluoro- and 0.7 g of 5-chloro-2-phenyl-4H-3,1-benzoxazin-4-one of melting point 155°–159° C. The sulfolane distilled off contains a further 0.49 g of 5-fluoro-2-phenyl-4H-3,1-benzoxazin-4-one; the total amount is 13.6 g, corresponding to 72.7%.

EXAMPLE 7

A mixture of 20 g of 5-chloro-2-phenyl-4H-3,1-benzoxazin-4-one, 68 g of sulfolane and 5 g of thionyl chloride is stirred for 30 minutes at 100° C., after which the pressure is reduced to 22 mbar at no higher than 102° C. for 30 minutes. 6.35 g of potassium fluoride treated with thionyl chloride, and 0.25 g of iodine, are then added, under a layer of nitrogen, and stirring is then continued for 2 hours at 260° C.

Working up the reaction mixture as described in Example 1 gives 7.7 g of predominantly inorganic salts, 66 g of sulfolane and a mixture of 12.7 g of 5-fluoro-and 0.6 g of 5-chloro-2-phenyl-4H-3,1-benzoxazin-4-one of melting point 155°–159° C., in addition to a distillation residue of 4.6 g. The sulfolane distilled off contains a further 0.41 g of 5-fluoro-2-phenyl-4H-3,1-benzoxazin-4-one; the total amount is 13.1 g, corresponding to 70%.

EXAMPLE 8

A mixture of 200 g of 5-chloro-2-phenyl-4H-3,1-benzoxazin-4-one, 649 g of sulfolane and 60 g of thionyl chloride is stirred for 50 minutes at 100° C., after which the pressure is reduced to 28 mbar at no higher than 105° C. for 40 minutes. 63 g of potassium fluoride treated with thionyl chloride, and 1 g of iodine, are added, under a layer of nitrogen, and stirring is then continued at 220° C.. After 4 1/4 hours, a further 13.5 g of potassium fluoride (total amount 76.5 g) and 2 g of iodine are added, and after a total of 6 hours a further 0.5 g of iodine (total amount 3.5 g) is introduced; the total reaction time is 12 hours. The reaction mixture is diluted with 1,2-dichloroethane at 75° C., and then worked up as described in Example 4 to give 96 g of predominantly inorganic salts, 640 g of sulfolane and a mixture of 152.9 g of 5-fluoro- and 5.1 g of 5-chloro-2-phenyl-4H-3,1-benzoxazin-4-one of melting point 157°–161° C., in addition to a distillation residue of 19.8 g. The sulfolane distilled off contains a further 3.2 g of 5-fluoro-2-phenyl-4H-3,1-benzoxazin-4-one; the total amount is 156.1 g, corresponding to 83.4%.

EXAMPLE 9

50 g of 5-chloro-2-phenyl-4H-3,1-benzoxazin-4-one and 13.53 g of dry potassium fluoride are introduced, while stirring, into a flask which has been heated to 260° C. and flushed with nitrogen. The reaction mixture is heated to 380° C. in the course of 4 minutes, and stirring is continued for 25 minutes while the course of the reaction is monitored by gas chromatography. The mixture is worked up by taking it up in methylene chloride and filtering off the inorganic precipitate under suction. The filtrate is freed from methylene chloride at 50° C./14 mbar in a rotary evaporator, and the residue is distilled over a heated bridge at a bath temperature as high as 230° C./0.3 mbar to give 38.1 g of a virtually colorless product which has a melting point of 160°–162° C. and consists of 37.68 g (80.5% of theory) of 5-fluoro-and 0.42 g (0.8% of theory) of 5-chloro-2-phenyl-4H-3,1-benzoxazin-4-one.

EXAMPLE 10

The reaction is carried out under the same conditions as in Example 9, except that 11.95 g of the potassium fluoride pretreated as described in Example 3a are used and stirring is continued for 27 minutes at 380° C. Working up gives 40.6 g of a virtually colorless distillate which has a melting point of 150°–156° C. and consists of 36.13 g (77.2% of theory) of 5-fluoro- and 4.47 g (8.9% of theory) of 5-chloro-2-phenyl-4H-3,1-benzoxazin-4-one.

EXAMPLE 11

A mixture of 20 g of 5-chloro-2-phenyl-4H-3,1-benzoxazin-4-one and 6.27 g of the potassium fluoride pretreated as described in Example 3a is stirred for 21 hours at 300° C. Working up as described in Example 9 gives 15.6 g of a virtually colorless distillate which has a melting point of 155°–160° C. and consists of 14.85 g (79.3% of theory) of 5-fluoro-2-phenyl-4H-3,1-benzoxazin-4-one and 0.75 g (3.7% of theory) of the starting compound.

EXAMPLE 12

44 g of 5-chloro-2-phenyl-4H-3,1-benzoxazin-4-one are mixed with 11.15 g of dry potassium fluoride under a layer of nitrogen, in the course of 3 minutes, at 350° C., after which the mixture is kept at 350° C. for 1½ hours. Working up as described in Example 9 gives 35.6 g of a virtually colorless distillate which has a melting point of 158°–160° C. and consists of 34.21 g (82.9% of theory) of 5-fluoro-2-phenyl-4H-3,1-benzoxazin-4-one and 1.39 g (3.2% of theory) of the 5-chloro compound.

EXAMPLE 13

12.4 g of potassium fluoride are dried for 20 minutes at 330° C./14 mbar in a stirred apparatus. The apparatus is flushed with nitrogen, 50 g of 5-chloro-2-phenyl-4H-3,1-benzoxazin-4-one are added at 290° C., while stirring, and the mixture is then heated at 330° C. Stirring is initially continued for 10 minutes at this temperature, after which the mixture is kept at 330° C. for 1½ hours without further stirring. The pressure is reduced to 212 mbar and the lower-boiling component is distilled off continuously under reflux at 284°–302° C. and a bath temperature of 345° C., over an intermediate, externally heated column possessing a distillation head. During this procedure, the internal temperature falls temporarily to 315° C.; the duration of the distillation, which is included as part of the total reaction time, is set at 1¼ hours, the pressure being reduced to 14 mbar toward the end of the reaction. 43.4 g of a virtually colorless distillate which has a melting point of 147°–158° C. and consists of 38.1 g (81.3% of theory) of 5-fluoro-2-phenyl-4H-3,1-benzoxazin-4-one and 5.2 g (10.4% of theory) of the 5-chloro compound are obtained. The gray distillation residue (18.3 g) which is in the form of a powder is freed from the inorganic salts by washing with water and is dried, 3.2 g of a brown powder remaining as a residue.

EXAMPLE 14

A mixture of 50 g of 5-chloro-2-phenyl-4H-3,1-benzoxazin-4-one and 12.4 g of potassium fluoride is passed, in the course of 14 minutes, through a tube heated at 420°–430° C. in an electrical tube furnace and is then distilled from a connected distillation apparatus at 240°–244° C./15 mbar. 39.5 g of a virtually colorless distillate which has a melting point of 144°–156° C. and consists of 35.15 g (75% of theory) of 5-fluoro-2-phenyl-4 H-3,1-benzoxazin-4-one and 4.35 g (8.7% of theory) of the unreacted starting material are obtained.

EXAMPLE 15

4.2 g of molten 5-chloro-2-phenyl-4H-3,1-benzoxazin-4-one are vaporized continuously in a stream of nitrogen at 450° C. in the course of 10 minutes, and passed at the same temperature through a tube furnace, together with 9.47 g of potassium fluoride. The distillate is washed with petroleum ether, and 3.1 g of a mixture which has a melting point of 139°–147° C. and consists of 2.39 g (60.6% of theory) of 5-fluoro-2-phenyl-4H-3,1-benzoxazin-4-one and 0.71 g (16.9% of theory) of the 5-chloro compound are obtained.

EXAMPLE 16

A mixture of 20 g of 5-chloro-2-phenyl-4H-3,1-benzoxazin-4-one, 6 g of the potassium fluoride pretreated as described in Example 3a and 0.3 g of sodium iodide is stirred for 3 hours at 330° C. Subsequent distillation over a heated bridge gives 15.4 g of a virtually colorless distillate which has a melting point of 162°–164° C. and consists of 15.29 g (81.7% of theory) of 5-fluoro-2-phenyl-4H-3,1-benzoxazin-4-one and 0.11 g (0.6%) of the unreacted starting material.

We claim:

1. A process for the preparation of a 5-fluoro-2-phenyl-4H-3, 1 benzoxazin-4-one (I)

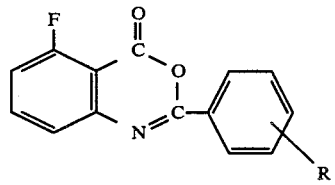

where R is hydrogen, halogen, $C_1$–$C_3$–alkyl, or trifluoromethyl, trifluoromethoxy, chlorodifluoromethoxy, difluoromethoxy, tetrafluoroethoxy, trifluoromethylmercapto or chlorodifluoromethylmercapto in the m- or p-position which comprises reacting a corresponding 2-phenyl-4H-3,1-benzoxazin-4-one (II)

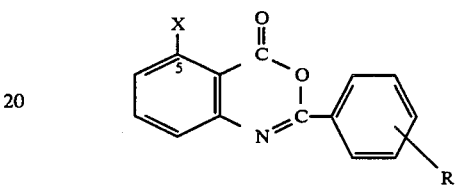

where X is chlorine, bromine, iodine, nitro, mesyl or tosyl, with an alkali metal fluoride, said reaction being carried out in the absence of water.

2. The process of claim 1, wherein X is chlorine or bromine.

3. The process of claim 2, wherein one or more of the starting materials are pretreated with an acid halide which decomposes to give gaseous substances.

4. The process of claim 3, wherein the pretreatment is carried out at no higher than 120° C.

5. The process of claim 3, wherein the reaction is carried out in the presence of the acid halide.

6. The process of claim 2, wherein thionyl chloride is used as the acid halide.

7. The process of claim 2, wherein potassium fluoride is used as the alkali metal fluoride.

8. The process of claim 2, wherein the reaction is carried out in a solvent at from about 150° to 250° C.

9. The process of claim 2, wherein an aliphatic sulfone is used as the solvent.

10. The process of claim 2, wherein the reaction is carried out in the presence of a catalyst which acts as a solubilizer.

11. The process of claim 2, wherein the reaction is carried out in the presence of a metal iodide and/or iodine, the temperature of the reaction is 160°–280° C., and the metal iodide and/or iodine are added during the reaction.

12. The process of claim 11, wherein the reaction temperature is from 180°–260° C.

13. The process of claim 2, wherein the reaction is carried out essentially in the absence of a solvent, at above 250° C.

14. The process of claim 13, wherein the reaction is carried out at from 300° to 500° C.

15. The process of claim 11, wherein the reaction is carried out in the presence of a metal iodide, at from 300° to 400° C.

16. The process of claim 2, wherein the 5-fluoro-2-phenyl-3,1-benzoxazin-4-one formed during the reaction is removed continuously from the reaction mixture.

17. The process of claim 2, wherein, after initial thorough mixing of the reactants, the reaction is carried out essentially without stirring, by a type of baking process.

18. The process of claim 2, wherein the reaction is carried out in a tube reactor.

* * * * *